United States Patent [19]

Arndt et al.

[11] Patent Number: 5,602,284
[45] Date of Patent: Feb. 11, 1997

[54] PROCESS FOR SEPARATING OFF AMINOBIPHENYL FROM DIPHENYLAMINE

[75] Inventors: Frank Arndt; Hans-Josef Buysch, both of Krefeld; Rudolf Wiemers, Meerbusch, all of Germany

[73] Assignee: Bayer Aktiengesellschaft, Leverkusen, Germany

[21] Appl. No.: 526,146

[22] Filed: Sep. 11, 1995

[30] Foreign Application Priority Data

Sep. 13, 1994 [DE] Germany ............ 44 32 554.1
Sep. 13, 1994 [DE] Germany ............ 44 32 553.3
Sep. 19, 1994 [DE] Germany ............ 44 33 265.3
Oct. 25, 1994 [DE] Germany ............ 44 38 003.8
Oct. 26, 1994 [DE] Germany ............ 44 38 173.5

[51] Int. Cl.$^6$ ............................................. C07C 209/86
[52] U.S. Cl. ...................... 564/433; 564/307; 564/435; 564/437
[58] Field of Search ............................ 564/307, 433, 564/435, 437

[56] References Cited

U.S. PATENT DOCUMENTS

| | | | |
|---|---|---|---|
| 2,256,196 | 9/1941 | Filbert | 260/576 |
| 3,849,495 | 11/1974 | Bromby | 564/429 |
| 5,107,024 | 4/1992 | Kool et al. | 564/433 |
| 5,481,037 | 1/1996 | Fuchs et al. | 564/437 |

FOREIGN PATENT DOCUMENTS 396929  1/1966  Switzerland.

*Primary Examiner*—Richard L. Raymond
*Attorney, Agent, or Firm*— Sprung Horn Kramer & Woods

[57] ABSTRACT

Aminobiphenyl (ABP) can be separated off from diphenylamine (DPA) by treating the DPA to be purified at elevated temperature with a substance in which oxygen is bonded by a double bond to a C atom, an N atom or another O atom and then separating off the DPA from the treated mixture.

10 Claims, No Drawings

PROCESS FOR SEPARATING OFF AMINOBIPHENYL FROM DIPHENYLAMINE

BACKGROUND OF THE INVENTION

1. Field of the Invention

The present invention relates to a process for separating off aminobiphenyl (ABP) from diphenylamine (DPA), which is characterized in that a substance in which oxygen is bonded by a double bond to a C atom, an N atom or another O atom is allowed to act at elevated temperature on DPA containing ABP and then the DPA is separated off.

DPA is an industrial product which, owing to its production process (Ullmann's Encyclopedia of Technical Chemistry, 4th Ed., Vol. 7, pp. 573ff; Kirk-Othmer's Encyclopedia of Chemical Technology, 4th Ed., Vol. 2, pp. 452ff) is contaminated with small amounts of ABP. The isomeric ABPs, in particular 4-ABP, have been shown to be carcinogenic and therefore must be removed as completely as possible from DPA.

2. Description of the Related Art

To remove ABP from DPA it is proposed in U.S. Pat. No. 5,107,524 to treat contaminated DPA in dissolved form with an ion exchanger. Although this procedure leads to success it is laborious and complex. Thus a prepurified DPA already freed as far as possible of coarse contaminants by distillation must be used. In addition, a solvent is required which must be removed again after the treatment. Furthermore still, the ion exchanger requires regeneration with acid after it is completely loaded with the toxic ABP. This in turn generates problems in the handling and disposal of the ABP waste liquors.

There was therefore still a requirement to provide a simple and effective process for removing ABP from DPA.

SUMMARY OF THE INVENTION

Surprisingly, it has been found that this succeeds in an outstanding manner if a DPA contaminated with ABP is treated at elevated temperature with a substance in which oxygen is bonded by a double bond to a C atom, an N atom or another O atom.

A process has been found for separating off aminobiphenyl from diphenylamine which is characterized in that the diphenylamine to be purified is treated at 50° to 310° C. with 1 to 10,000 mol of a substance containing double-bonded oxygen of the formula $$A=O \qquad (I),$$

in which

A represents the $C_1$–$C_{20}$ radical of a carbonyl compound selected from the group consisting of saturated and unsaturated, open-chain or cyclic, aliphatic or aromatic aldehydes, ketones and quinones, the $C_1$–$C_{30}$ radical of an aliphatic, aromatic or araliphatic mono- or polycarboxylic acid or one of its derivatives, the radical of a carbonic acid derivative, the radical of a nitroso compound or an oxygen atom, per mole of aminobiphenyl present and then the diphenylamine is separated off from the treated mixture.

DETAILED DESCRIPTION OF THE INVENTION

The radical A is thus defined in such a way that, together with the double-bonded oxygen, it gives the respective substance mentioned; thus acetone is obtained from A in the meaning $(CH_3)_2C$ together with the double-bonded oxygen, succinic acid is obtained from A in the meaning HOOC—$CH_2$—CH—C(OH) and phosgene is obtained from A in the meaning $Cl_2C$.

Obviously, substances can also be used according to the invention which contain or form substances of the formula (I).

Carbonyl compounds A=O (I) in the context of the present invention are aldehydes, ketones and quinones of the aliphatic and aromatic series having 1 to 20, preferably 1 to 15, particularly preferably 1 to 10, C atoms.

An inexhaustive listing of suitable carbonyl compounds is as follows: benzoquinone, naphthoquinone, anthraquinone, diphenoquinone, toluquinone, xyloquinone, quinone methide, acetone, methyl ethyl ketone, diethyl ketone, dipropyl ketone, dibutyl ketone, methyl butyl ketone, cyclopentanone, cyclohexanone, methylcyclohexanone, isopropylcyclohexanone, tert-butyl-cyclohexanone, mesityl oxide, phorone, isophorone, acetylacetone, ethyl acetoacetate, acetophenone, benzoin, benzil, formaldehyde, acetaldehyde, propionaldehyde, butyraldehyde, valeraldehyde, capronaldehyde, acrolein, crotonaldehyde, propiolaldehyde, benzaldehyde, salicylaldehyde, tolylaldehyde, chlorobenzaldehyde, cinnamaldehyde, furfural, glycolaldehyde, oxaldialdehyde, glutardialdehyde, chloroacetaldehyde, chloropropionaldehyde. Carbonyl compounds having two or more carbonyl groups in the molecule, in the context of the invention, are calculated as two or more, as appropriate, moles of carbonyl compound.

Among the carbonyl compounds listed, the following are preferred: benzoquinone, naphthoquinone, toluquinone, acetone, methyl ethyl ketone, cyclohexanone, mesityl oxide, isophorone, acetylacetone, benzil, formaldehyde, acetaldehyde, propionaldehyde, acrolein, crotonaldehyde, benzaldehyde, salicylaldehyde, furfural, glycolaldehyde, oxaldialdehyde, glutardialdehyde.

Aldehydes and ketones are preferably used, particularly preferably aldehydes.

Suitable carboxylic acids of the formula A=O (I) in which the carbon atom which bears the double-bonded oxygen additionally has an OH group are aliphatic, aromatic and araliphatic mono- and polycarboxylic acids having 1 to 30 C atoms, preferably 2 to 20, particularly preferably 2 to 16, C atoms. Suitable derivatives of the carboxylic acids are esters thereof with aliphatic, aromatic and araliphatic mono- and polyhydroxy compounds having 1 to 30, preferably 1 to 20, particularly preferably 1 to 16, C atoms, in addition their amides with ammonia, primary and secondary aromatic amines with in total 6 to 18, preferably 6 to 12, C atoms, their halides, preferably chlorides, and their anhydrides. In the derivatives, in an analogous manner to the acids, the carbon atom which bears the double-bonded oxygen additionally bears the acid derivative group.

The carboxylic acids can be substituted by halogen, preferably by chlorine or by hydroxyl, and can contain olefinic or acetylenic multiple bonds. Their aromatic moieties can be diphenyl ether or benzophenone groups.

Those which may be mentioned by way of example are acetic acid, propionic acid, butyric acid, valeric acid, caproic acid, dodecanoic acid, pentadecanoic acid, stearic acid, benzoic acid, toluic acid, chlorobenzoic acid, salicylic acid, oleic acid, linoleic acid, cyclohexanecarboxylic acid, maleic acid, succinic acid, tartaric acid, malic acid, aconitic acid, adipic acid, azelaic acid, dodecanedioic acid, citric acid, alkylsuccinic acids, terephthalic acid, isophthalic acid, o-phthalic acid, acrylic acid, methacrylic acid, cinnamic acid, lactic acid, chloroacetic acid, chloropropionic acid, propiolic acid, phenylpropiolic acid, trimesic acid, pyromellitic acid, diphenyl ether dicarboxylic acid, diphenyl ether tetracarboxylic acid, of the polycarboxylic acids preferably 1,2-dicarboxylic acids; acid chlorides of such carboxylic acids; their open-chain or cyclic anhydrides or oligo-or polyanhydrides, if such can be formed, preferably the cyclic anhydrides, in addition oligomers having molecular weights up to 20,000, preferably up to 10,000, of acrylic acid, methacrylic acid, maleic acid (maleic anhydride), aconitic acid (aconitic anhydride) or their copolymers with styrene, vinyl acetate, ethylene, butadiene and acrylonitrile. Suitable hydroxyl compounds for the esters of such carboxylic acids which may be mentioned are: methanol, ethanol, butanol, hexanol, cyclohexanol, hexane diol, ethylene glycol, propylene glycol, glycerol, pentaerythritol, neopentyl glycol, phenol, cresol, xylenol, hydroquinone, resorcinol, dihydroxybiphenyl, dihydroxydiphenyl ether, bisphenol A, preferably $C_1$–$C_4$-alcohols and phenol. Amines for the amides of the said carboxylic acids which may be mentioned are: aniline, toluidine, diphenylamine, xylidine, methyldiphenylamine and hydroxydiphenylamine. Preferably, in addition to ammonia, diphenylamine is also used.

Preferably, a derivative of a carboxylic acid is used, particularly preferably an anhydride, an ester or an amide, very particularly preferably an anhydride or an ester or amide having an aromatic group in the acid or in the ester or amide moiety.

Suitable compounds of carbonic acid as substances of formula (I) are monomeric carbonic acid derivatives with 1 to 38 C atoms, preferably 1 to 28 C atoms, and polymeric carbonic acid derivatives with molar weight of up to 50,000, preferably up to 30,000, especially up to 10,000.

Suitable are therefore:

phosgene, chloroesters (II) thereof and esters (III) thereof with radicals of aliphatic, araliphatic and aromatic hydroxyl compounds $R^1$ and $R^2$, which latter, independently of one another, can contain 1 to 20, preferably 1 to 18, particularly preferably 1 to 15 C atoms:

$$ClCOOR^1 \text{ (II) and } R^1O\text{—}CO\text{—}OR^2 \quad \text{(III)},$$

respectively;

unsubstituted urea and monosubstituted to tetrasubstituted urea (IV), where the individual substituents $R^3$–$R^6$ can be identical or different and can be hydrogen or can contain 1 to 20, preferably 1 to 16, particularly preferably 1 to 12, C atoms and can be of aliphatic, araliphatic or aromatic nature:

aliphatic, araliphatic and aromatic monoisocyanates or polyisocyanates (V), (VI) and (VII), respectively, having aliphatic, araliphatic or aromatic radicals $R^7$, $R^8$ and $R^9$ with 1 to 38, preferably 1 to 28, particularly preferably 1 to 20, C atoms:

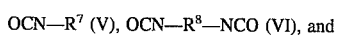

$OCN\text{—}R^7$ (V), $OCN\text{—}R^8\text{—}NCO$ (VI), and

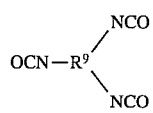

respectively;

acyl isocyanates, chlorocarbonyl isocyanate and chlorosulphonyl isocyanate;

urethanes (VIII) monosubstituted to trisubstituted with aliphatic, araliphatic and aromatic radicals $R^{10}$, $R^{11}$ and $R^{12}$ having 1 to 24, preferably 1 to 18, particularly preferably 1 to 15, C atom, wherein $R^{11}$ and $R^{12}$ in addition and independently of one another can denote hydrogen:

in addition allophanates, isoureas, uretdiones, uretonimines, carbodiimides, biurets, polyurets, derived from the compounds specified above.

Suitable compounds of carbonic acid are therefore chloroesters, monoesters, oligoesters and polyesters thereof with aliphatic, araliphatic and aromatic mono- and oligo-hydroxyl compounds which can contain 1 to 20, preferably 1 to 18, particularly preferably 1 to 15, C atoms. Those which may be mentioned by way of example are the esters of methanol, ethanol, propanol, butanol, benzyl alcohol, phenol and cresol, the cyclic esters and polyesters of ethylene glycol, propylene glycol, glycerol, butane diol, hexane diol, diglycol, triglycol, neopentyl glycol, trimethylolpropane, cyclohexanedimethanol, bisphenol A, dihydroxybiphenyl, pyrocatechol, resorcinol, hydroquinone, bisphenol F, dihydroxydiphenyl ether and dihydroxydiphenyl sulphide.

Also suitable are monoureas and oligoureas whose hydrogen atoms on the N atom can be partly or completely substituted by alkyl, aralkyl or aryl radicals and contain, per urea group, 0 to 20, preferably 0 to 16, and particularly preferably 0 to 12, C atoms as aliphatic, araliphatic or aromatic groups. Those which may be mentioned by way of example are urea itself, then the ureas of methylamine, ethylamine, propylamine, butylamine, cyclohexylamine, benzylamine, dimethylamine, diethylamine, dibutylamine, of aniline and diphenylamine, the cyclic and oligomeric ureas of ethylenediamine, propylenediamine, butylenediamine, hexamethylenediamine and dodecamethylene-diamine.

Additionally suitable are monoisocyanates and oligoisocyanates having 1 to 38, preferably 1 to 28, particularly preferably 1 to 20, C atoms of aliphatic, araliphatic and aromatic nature per isocyanate group. Those which may be mentioned by way of example are the isocyanates of methyl-, ethyl-, propyl-, isopropyl-, butyl-, amyl-, cyclohexyl-, lauryl-, stearyl- and benzylamine, of aniline, toluidine, toluylenediamine, hexamethylenediamine, naphthylenediamine, isophoronediamine, methylenedianiline and oligomers thereof.

Urethanes from the above-specified mono- and oligoisocyanates are also suitable, for example with the following monohydroxy and oligohydroxy compounds: methanol, ethanol, propanol, butanol, isopropanol, isobutanol, cyclohexanol, 1,4-butanediol, ethylene glycol, propylene glycol, 1,6-hexanediol, neopentyl glycol, phenol, cresol, xylenol, tert-butylphenol, chlorophenol, hydroquinone, pyrocatechol, bisphenol F, bisphenol A, bisphenol Z, dihydroxydiphenyl sulphide, novolaks, in addition glycerol, trimethylolpropane, pentaerythritol and sugars. Preference is given to the urethanes from monoisocyanates with monohydroxy and oligohydroxy compounds, from monohydroxy compounds with monoisocyanates and oligoisocyanates and from diisocyanates and dihydroxy compounds.

Suitable compounds are, in addition, allophanates and isoureas of the formulae:

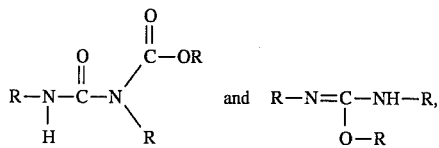

derived from the abovementioned monoisocyanates and oligoisocyanates and the abovementioned monohydroxy and oligohydroxy compounds, and furthermore Uretides 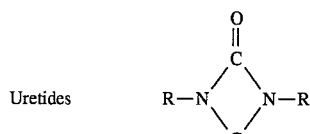

Uretonimines 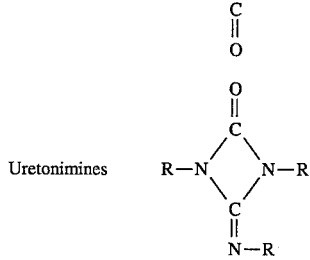

Carbodiimides 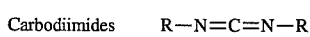

Biurets 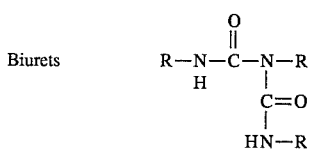

Polyurets 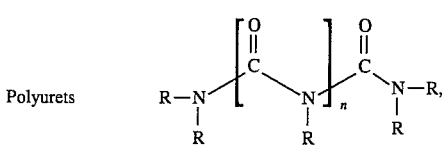

derived from the abovementioned monoisocyanates and oligoisocyanates where R can be identical or different and can be an aliphatic or aromatic $C_1$–$C_{12}$ radical and n denotes an integer from 1–50.

Preferably, the following are used according to the invention: ureas, isocyanates, aromatic carbonates and aromatic urethanes. Particular preference is given to: urea, diphenyl carbonate, isocyantes based on aniline, toluidine, toluylenediamine, methylenedianiline and oligomers and urethanes thereof from the said aromatic isocyanates and phenol.

The above-specified compounds of carbonic acid are known and are described, for example, in Houben-Weyl, Methoden der organischen Chemie [Methods of Organic Chemistry], 4th edition, Volume E4; Kirk-Othmer, Encycl. of Chem. Techn. 3. Ed., Vol. 13, pp. 789ff; Ullmann's Encycl. of Ind. Chem. 5th Ed., Vol A14, pp. 611ff and Vol. A5, pp. 197ff.

Nitroso compounds as substances A=O (I) are those which contain the group —N=O. It can be bonded to the rest of the molecule via a C atom, an N atom or an O atom.

Suitable nitroso compounds are therefore aliphatic, cycloaliphatic, araliphatic, aromatic and heterocyclic nitroso compounds with 1 to 25 C atoms, preferably 1 to 18 C atoms. Those which may be mentioned by way of example are nitrosomethylcyclohexane, nitroso-isobutane, nitrosocarboxylic acids such as α-nitrosoisobutyric acid, diethyl α-nitrosomalonate and o-nitrosobenzoic acid, nitrosohalides such as 1-nitroso-1-chloro-cyclohexane, 2-nitroso-3-chlorobutane and 1-nitroso-2-chloro-cyclohexane, nitrosobenzene, nitrosophenol, nitroso-N,N-dimethylaniline, but also nitrosoheterocycles, such as 5-nitroso-2-amino-4-methyl-1,3-thiazole, nitroso-antipyrine or 4-amino-1,3-dimethyl-5-nitroso-uracil of the following formulae:

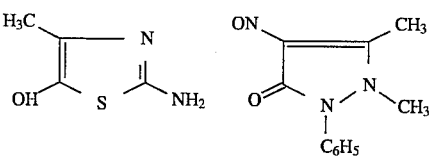

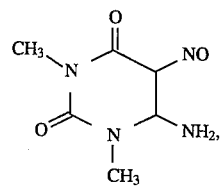

Nitrosolic acids having the group:

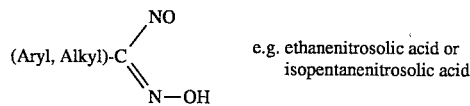

and pseudonitrols having the group

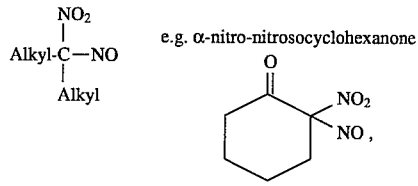

in addition, compounds which contain the nitroso group bound via an N atom such as nitrosamines, nitrosamides, nitrosoureas, nitrosoguanidines, isonitramides, nitrosohydroxylamines. Those which may be mentioned are, e.g. dimethyl-nitrosamine, dicyclohexyl-nitrosamine, dibenzylnitrosamine, diphenylnitrosamine, N-nitrosomethylacetamide, N-nitrosobutylbenzamide, N-nitrosophenyl-isobutyramide, N-nitroso-N-methyltosylamide, N-nitrosocaprolactam, N-nitroso-N-butyl-urea, N-nitroso-N-ethylurethane, N-nitroso-N-methyl-guanidine and nitrosation products of urotropin such as 3,7-dinitroso-1,3,5,7-tetraaza-bicyclo[3,3,1]nonane,

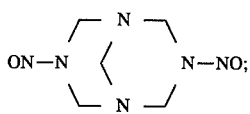

N-nitrosophenylhydroxamine or, for example, salts of methylene diisonitramide

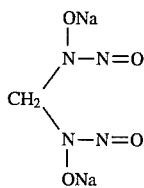

in addition, compounds which contain the nitroso group bound via an O atom such as nitrous acid and its esters methyl nitrite, ethyl nitrite, isopropyl nitrite and isoamyl nitrite.

Since nitroso compounds frequently occur in the form of their dimers, these, if they can be formed, are also included under nitroso compounds suitable for the process according to the invention.

Finally, compounds are suitable which can produce organic nitroso compounds such as nitrogen oxide, $NO_2$, $N_2O_4$, $N_2O_3$, $N_2O_5$, nitrosyl chloride and nitrosyl sulphuric acid. Finally, nitrous acid, for example in the form of its alkali metal salts, is useful; from such salts, the nitrous acid can be liberated using stronger acids. In the following, such compounds are likewise described as nitroso compounds.

For the case of the use of oxygen as the substance A=O (I), this can be used in pure form, but preferably in mixtures with inert gases, such as hydrogen, water vapour, carbon monoxide, carbon dioxide, low hydrocarbons or nitrogen. Particular preference is given to use in a mixture with nitrogen, very particular preference to use in the form of atmospheric air.

Oxygen-releasing compounds in the meaning according to the invention are those which contain oxygen in a peroxide bond. Those which may be mentioned by way of example are hydrogen peroxide, for example in a mixture with water or organic inert solvents such as alcohols; sodium peroxide; perborates, such as sodium perborate and perborax, ketone peroxides, such as acetone peroxide or cyclohexanone peroxide; acyl peroxides, such as peracetic acid, perpropionic acid; diacyl peroxides, such as dibenzoyl peroxide. Other compounds which are useful are alkyl hydroperoxides and peroxides and aralkyl hydroperoxides and peroxides such as cyclohexyl hydroperoxide, tert-butyl hydroperoxide, cumyl hydroperoxide, p-isopropylcumyl hydroperoxide, $\alpha,\alpha'$-di-hydroperoxy-diisopropylbenzene, di-tert-butyl peroxide, dicumyl peroxide, tert-butyl-cumyl peroxide, $\alpha,\alpha'$-di-tert-butyl-peroxy-diisopropylbenzene. Other inorganic peroxy compounds are, for example, peroxychromates, peroxyniobates, peroxytantalates, peroxytungstates, peroxymolybdates, peroxyvanadates, peroxytitanates, peroxysulphates and peroxyphosphates. Finally, hydrogen peroxide can also be used as an addition compound to urea.

The said oxygen-releasing compounds are generally used in dilute form. Diluents are, for example, water or inert organic compounds, for example alcohols, such as methanol, isopropanol, tert-butanol; ketones, such as acetone, methyl ethyl ketone, methyl isopropyl ketone or methyl tert-butyl ketone; carboxylic acids, such as acetic acid or propionic acid; acid amides, such as dimethylacetamide or N-methylpyrrolidone.

Preferably, however, oxygen is used in particular in a mixture with nitrogen.

Of the listed substances containing double-bonded oxygen of the formula A=O (I), those are preferred in which the oxygen is bonded by a double bond to a C atom. These preferred substances are therefore those in which A represents the $C_1$–$C_{20}$ radical of a carbonyl compound selected from the group consisting of saturated and unsaturated, open-chain or cyclic, aliphatic or aromatic aldehydes, ketones and quinones, the $C_1$–$C_{30}$ radical of an aliphatic, aromatic or araliphatic monocarboxylic or polycarboxylic acid or one of the derivatives thereof or the radical of a carbonic acid derivative.

Particularly preferred substances are those in which A represents the radical of one of the said monocarboxylic or polycarboxylic acids or one of the derivatives thereof, the radical of an aldehyde or the radical of a carbonic acid derivative. In very particularly preferred substances, A represents the radical of a carbonic acid derivative or the radical of an aldehyde.

To separate off the ABP, the treatment with at least 1 mol of substance of the formula A=O (I) per mole of ABP is necessary. In order to achieve as complete as possible a separation of the ABP, an excess of the substance of the formula (I) however is advantageously used, which, in particular to cover trace amounts of ABP includes very great excesses of substance of the formula (I). However, such great excesses of substance of the formula (I) in the case of small amounts of ABP still represent, in absolute terms, a small amount, based on the amount of the DPA to be purified. The amount of substance of the formula (I) is therefore 1 to 10,000 mol, preferably 5 to 10,000 mol, particularly preferably 15 to 7000 mol, very particularly preferably 30 to 3000 mol, per mole of ABP to be removed.

The treatment is carried out at a temperature of 50 to 310, preferably 60° to 250° C., particularly preferably 60° to 200° C.

The treatment time is a few minutes to several hours, for example 5 minutes to 10 hours, preferably 1 to 6 hours, and is not critical per se. In fact, a check may readily be made analytically in the individual case of what time is necessary in combination with a selected temperature in order to remove ABP as completely as possible.

The process according to the invention can be carried out discontinuously or continuously. For this purpose, for example, a reaction product from the preparation of DPA is first partially or completely freed of low-boilers, for example aniline, by distillation and the crude product present in the liquid phase is admixed with the amount of substance of the formula (I) calculated according to the content of ABP in the context of the above-specified molar ratios and then stirred in a vessel at the chosen reaction temperature. It is also possible to add the substance of the formula (I) before the low boilers, especially aniline, has been distilled off. A predistilled crude product can also be admixed with the substance of the formula (I) in a continuous manner and then be continuously exposed to an elevated temperature in a delay vessel or a delay tube. Low-boiling substances of the formula (I) can be added in vapourized form to the DPA to be purified; otherwise, addition is possible in solid form, liquid (molten) form or in the form dissolved in an inert solvent. Suitable addition devices are, for example, nozzles, gas-introducing stirrers, controllable feed reservoirs, pumps and others known to those skilled in the art. A continuous process using gaseous or vapourized substances of the formula (I) can be carried out in apparatuses such as stirred tanks, reactors having gas-introducing stirrers, bubble columns or trickle-film columns; the substance of the formula (I) is introduced in this case into the liquid DPA via nozzles or other distribution elements for gaseous substances. In this case, atmospheric pressure or elevated pressure can be employed, for example 1 to 25 bar, preferably 1 to 15 bar, particularly preferably 1 to 10 bar. Solid or liquid derivatives of carbonic acid can be added to the DPA as such or in dilution with an inert solvent. The treated mixture can, for example, be subjected to a crystallization or to a distillation to produce the purified DPA. Preferably, the DPA is separated off from the treatment mixture by distillation.

The process according to the invention can be applied both to crude DPA in a single-stage manner and also to a prepurified DPA, if appropriate in a multistage manner. Thus, for example, crude DPA can be initially prepurified with a relatively small amount, about 5 to 100 mol, of substance of the formula (I) per mole of ABP and then the prepurified DPA can be given a fine purification using an amount of 1000 to 7000 mol of substance of the formula (I) per mole of residual ABP which has been decreased.

The DPA freed of ABP obtained according to the invention is suitable for all applications, for example for the preparation of phenothiazines, rubber stabilizers or as an antioxidant preservative for fruits.

EXAMPLES 1 to 9

100 g of a crude DPA which was freed of low-boilers, particularly aniline (<0.1%) by distillation and contained 148 ppm of 4-ABP was admixed with a carbonyl compound and subjected to a temperature treatment for a certain time in a stirred flask under nitrogen. The flask contents were then distilled at 15 to 20 mbar and the distillate was analysed for ABP. Table 1 contains more detailed information and results.

TABLE 1

| Ex. | Carbonyl compound | Amount [g] | Temperature [°C.] | Time [h] | ABP ppm |
|---|---|---|---|---|---|
| 1 | Benzaldehyde | 1 | 150 | 3 | n.d. |
| 2 | Paraformaldehyde | 1 | 150 | 3 | n.d. |
| 3 | Paraformaldehyde | 0.5 | 150 | 3 | n.d. |
| 4 | Paraformaldehyde | 0.1 | 150 | 3 | n.d. |
| 5 | Furfural | 1 | 250 | 4 | n.d. |
| 5a | Furfural | 0.3 | 150 | 2 | 8 |
| 6 | Mesityl oxide | 1 | 200 | 4 | 10 |
| 7 | Crotonaldehyde | 1 | 180 | 4 | n.d. |
| 7a | Crotonaldehyde | 0.4 | 180 | 4 | n.d. |
| 8 | Benzil | 1 | 150 | 4 | 15 |
| 9 | Benzoquinone | 1.0 | 150 | 4 | 29 | n.d. = not detectable detection limit <5 ppm

EXAMPLES 10 to 12

100 g of a crude DPA which had been freed of low-boilers, particularly aniline (<0.1%) by distillation and contained 85 ppm of 4-ABP was aerated in a 250 ml flask with stirring. The flask contents were then distilled at 15 to 20 mbar and the amount of ABP present in the distillate was determined. Table 2 contains more detailed information.

TABLE 2

| No. | Air rate | Time (h) | Temperature | ABP ppm |
|---|---|---|---|---|
| 10 | 4 l/h | 3 | 250° C. | <10 |
| 11 | 3 l/h | 3 | 150° C. | 11 |
| 12 | 1 l/h | 4 | 200° C. | <5 |

EXAMPLES 13 and 14

If in an otherwise identical procedure the aeration was replaced by addition of peroxide, the results given in Table 3 are obtained.

TABLE 3

| No. | Peroxide | Time (h) | Temperature | ABP ppm |
|---|---|---|---|---|
| 13 | 1% by weight of benzoyl peroxide | 1 h +1 h +1 h | 50° C. 100° C. 150° C. | 18 |
| 14 | 1% by weight of tert-butyl hydroperoxide | 1 h +1 h +1 h | 50° C. 100° C. 150° C. | 13 |

EXAMPLES 15 to 17

100 g of a crude DPA which was freed of low-boilers, particularly aniline (<0.1%) by distillation and contained 148 ppm of 4-ABP was mixed with a nitroso compound in a 250 ml flask with stirring at approximately 80° C. and left at a certain temperature for some hours. The flask contents were then distilled at 15 to 20 mbar and the amount of ABP present in the distillate was determined. The following Table 4 contains more detailed information.

TABLE 4

| No. | g nitroso compound | Time [h] | Temperature | ABP [ppm] |
|---|---|---|---|---|
| 15 | 0.4 g NaNO$_2$ 0.4 g H$_3$PO$_4$ 1 g H$_2$O | 4 | 250 | <10 |
| 16 | 1 g of diphenylnitrosamine | 4 | 250 | 11 |
| 17 | 0.3 g of amyl nitrite | 3 | 170 | <10 |

EXAMPLES 18 to 23

50 g of crude diphenylamine freed of aniline and a carbonic acid derivative were heated in a 250 ml three neck flask at a predetermined temperature for some hours with stirring. The flask contents were then distilled at a pressure of 10 to 20 mbar and the content of 4-ABP in the distillate was determined. Table 5 shows the result.

TABLE 5

| No. | Carbonic acid derivative | g | Temp. | h | ppm 4-ABP |
|---|---|---|---|---|---|
| 18 | Urea | 0.4 | 180° | 4 | <5 |
| 19 | Diisocyanatodiphenyl-methane | 0.5 | 160° | 3 | <5 |
| 20 | Hexamethylene diisocyanate | 0.5 | 155° | 3 | <5 |
| 21 | Hexamethylene diisocyanate | 0.3 | 140° | 2 | 14 |
| 22 | Diphenyl carbonate | 0.5 | 100° 150° 180° | 1 2 2 | 20 |
| 23 | Phenyl chlorocarbonate | 0.5 | 100° 150° 180° | 1 2 2 | 6 |

EXAMPLE 24

500 g of crude diphenylamine freed of aniline and 2.0 g of diisocyanato-diphenylmethane (MDI) were heated at 150° C. for 4 h with stirring and were then distilled over a column at 10 mbar. A colourless distillate of 478 g was obtained having a content of aminobiphenyl of <5 ppm and approximately 20 g of residue.

EXAMPLE 25

Example 24 was repeated using 2.0 g of urea instead of MDI. The result of the distillation was equal to that of Example 24. The content of ABP was likewise <5ppm.

EXAMPLES 26 to 35

100 g of crude diphenylamine (DPA) which had been freed of aniline (<0.1%) by distillation and contained 125 ppm of 4-aminobiphenyl (ABP) were mixed with a carboxylic acid derivative in the 250 ml flask with stirring at 80° C. and then heated for some hours at the intended temperature. The flask contents were then distilled at 15 to 20 mbar and the amount of ABP present in the distillate was determined. Table 6 has the results.

TABLE 6

| No. | Carboxylic acid derivative (g) | h | °C. | ABP (ppm) |
|---|---|---|---|---|
| 26 | Phthalic anhydride 0.4 | 4 | 250 | <5 |
| 27 | Phthalic anhydride 0.4 | 4 | 150 | <5 |
| 28 | Pyromellitic dianhydride 0.4 | 4 | 150 | <5 |
| 29 | Pyromellitic dianhydride 0.4 | 4 | 180 | <5 |
| 30 | Pyromellitic dianhydride 1.0 | 3 | 150 | <5 |
| 31 | Diphenyl terephthalate 1.0 | 4 | 180 | <5 |
| 32 | Maleic anhydride 0.5 | 3 | 160 | <5 |
| 33 | N,N-Diphenylsuccinamic acid 0.8 | 5 | 180 | 10 |
| 34 | N,N-Diphenylacetamide 1.0 | 6 | 150 | 9 |
| 35 | Benzoyl chloride 1.0 | 5 | 180 | <5 |

EXAMPLE 36

500 g of crude DPA freed of aniline and containing 125 ppm of ABP, and 1 g of pyromellitic dianhydride were heated for 4 h at 150°; the mixture was then subjected to fractional distillation over a column at 9 to 10 mbar.

8 fractions of colourless distillate (in total 474 g) were obtained which all contained <5 ppm of ABP, and 21 g of residue were also obtained.

EXAMPLE 37

Example 24 was repeated but the diphenylamine still containing additionally 378 g aniline. After heating 4 h at 185° C. the aniline was separated by vacuum distillation and thereafter the purified DPA was distilled. All fractions obtained had a content of ABP of <5ppm.

Comparison example

A repetition of Example 36 without addition of pyromellitic dianhydride led to 8 fractions having increasing contents of ABP, beginning at 20 and ending at 670 ppm of ABP.

What is claimed is:

1. A process for separating off aminobiphenyl from diphenylamine, wherein the diphenylamine to be purified is treated at 50° to 310° C. with 1 to 10,000 mol of a substance containing double-bonded oxygen of the formula $$A=O \qquad (I),$$

in which

A represents the $C_1$–$C_{20}$ radical of a carbonyl compound selected from the group consisting of saturated and unsaturated, open-chain or cyclic, aliphatic or aromatic aldehydes, ketches and quinones, the radical of a non-substituted or substituted urea and the radical of a nitroso compound or an oxygen atom, per mole of aminobiphenyl present and then the diphenylamine is separated off from the treated mixture.

2. The process of claim 1, wherein A represents the radical of an aldehyde.

3. The process of claim 2, wherein the substance used is an aldehyde selected from the group consisting of formaldehyde, acetaldehyde, propionaldehyde, butyraldehyde, valeraldehyde, capronaldehyde, acrolein, crotonaldehyde, propiolaldehyde, benzaldehyde, salicylaldehyde, tolylaldehyde, chlorobenzaldehyde, cinnamaldehyde, furfural, glycolaldehyde, oxaldialdehyde, glutardialdehyde, chloroacetaldehyde and chloropropionaldehyde.

4. The process of claim 1, wherein the treatment is carried out at 60° to 250° C.

5. The process of claim 4, wherein the treatment is carried out at 60° to 200° C.

6. The process of claim 1, wherein 5 to 10,000 mol of substance A=O are used per mole of aminobiphenyl.

7. The process of claim 6, wherein 15 to 7,000 mol of substance A=O are used per mol of aminobiphenyl.

8. The process of claim 7, wherein 30 to 3,000 mol of substance A=O are used per mol of aminobiphenyl.

9. The process of claim 1, wherein the substance A=O used is a nitroso compound.

10. The process of claim 1, wherein the substance A=O used is oxygen.

* * * * *

UNITED STATES PATENT AND TRADEMARK OFFICE
CERTIFICATE OF CORRECTION

PATENT NO. : 5,602,284
DATED : February 11, 1997
INVENTOR(S) : Arndt, et al.

It is certified that error appears in the above-indentified patent and that said Letters Patent is hereby corrected as shown below:

Col. 12, line 23   Delete " ketches " and substitute -- ketones --

Signed and Sealed this

First Day of July, 1997

Attest:

Attesting Officer

BRUCE LEHMAN

Commissioner of Patents and Trademarks